United States Patent
Asogawa

(10) Patent No.: US 11,776,660 B2
(45) Date of Patent: Oct. 3, 2023

(54) INFORMATION PROCESSING APPARATUS, SUSPECT INFORMATION GENERATION METHOD AND PROGRAM

(71) Applicant: NEC Corporation, Tokyo (JP)

(72) Inventor: Minoru Asogawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/729,190

(22) Filed: Apr. 26, 2022

(65) Prior Publication Data

US 2022/0253650 A1 Aug. 11, 2022

Related U.S. Application Data

(63) Continuation of application No. 16/079,796, filed as application No. PCT/JP2017/007201 on Feb. 24, 2017, now Pat. No. 11,341,378.

(30) Foreign Application Priority Data

Feb. 26, 2016 (JP) .................................. 2016-035861

(51) Int. Cl.
*G16B 20/00* (2019.01)
*G06F 16/00* (2019.01)
(Continued)

(52) U.S. Cl.
CPC .............. *G16B 20/00* (2019.02); *G06F 16/00* (2019.01); *G06F 18/25* (2023.01); *G06Q 50/26* (2013.01);
(Continued)

(58) Field of Classification Search
CPC ............... G16B 20/00; G06K 9/00288; G06K 9/00892; G06K 9/00248; G06K 9/00281;
(Continued)

(56) References Cited

U.S. PATENT DOCUMENTS 9,116,882 B1  8/2015 Macpherson .......... G16B 40/00
9,734,163 B2  8/2017 Murakami et al.
(Continued)

FOREIGN PATENT DOCUMENTS

JP  05-143651 A   6/1993
JP  09-134428 A   5/1997
(Continued)

OTHER PUBLICATIONS

International Search Report of PCT/JP2017/007201 filed Apr. 25, 2017.
(Continued)

*Primary Examiner* — Edward F Urban
*Assistant Examiner* — Wassim Mahrouka

(57) ABSTRACT

An information processing apparatus includes an input, a blood-relative list generator, a similar image searcher, and a suspect information generator. The input receives DNA information of a suspect and facial image relating to a plurality of facial images. The blood relative list generator generates a list of blood relatives who are presumed to be blood relatives of the suspect from a plurality of pieces of DNA information. The similar image searcher calculates degree of similarity between facial images of persons on the blood-relative list and each of the plurality of facial images, and searches for and retrieves a facial image resembling the image of the person on the blood-relative list based on the calculated degree of similarity. The suspect information generation part generates suspect information by associating information relating to the retrieved facial image with information relating to the person on the blood-relative list who resembles the retrieved facial image.

7 Claims, 17 Drawing Sheets

(51) Int. Cl.
*G06Q 50/26* (2012.01)
*G06V 40/70* (2022.01)
*G06V 40/16* (2022.01)
*G06F 18/25* (2023.01)
*G06V 10/80* (2022.01)

(52) U.S. Cl.
CPC ............ *G06V 10/80* (2022.01); *G06V 40/165* (2022.01); *G06V 40/171* (2022.01); *G06V 40/172* (2022.01); *G06V 40/173* (2022.01); *G06V 40/70* (2022.01)

(58) Field of Classification Search
CPC .. G06K 9/00295; G06K 9/4609; G06F 16/00; G06Q 50/26
See application file for complete search history.

(56) References Cited

U.S. PATENT DOCUMENTS

| | | | |
|---|---|---|---|
| 2003/0225530 A1* | 12/2003 | Lowe | C12Q 1/6876 702/20 |
| 2004/0229231 A1 | 11/2004 | Frudakis et al. | |
| 2007/0037182 A1 | 2/2007 | Gaskin et al. | |
| 2008/0201327 A1* | 8/2008 | Seth | G06F 16/5854 707/999.005 |
| 2009/0060294 A1 | 3/2009 | Matsubara | G06K 9/00496 382/118 |
| 2010/0223281 A1 | 9/2010 | Hon | G16B 50/00 707/769 |
| 2011/0115937 A1 | 5/2011 | Sassa | G06K 9/00221 348/222.1 |
| 2013/0131994 A1 | 5/2013 | Birdwell | G16B 40/00 702/19 |
| 2014/0056509 A1 | 2/2014 | Nakashima et al. | |
| 2014/0278138 A1* | 9/2014 | Barber | G06F 16/24575 702/19 |
| 2015/0139492 A1 | 5/2015 | Murakami et al. | |

FOREIGN PATENT DOCUMENTS

| | | |
|---|---|---|
| JP | 10-115616 A | 5/1998 |
| JP | 2006-514553 A | 5/2006 |
| JP | 2010-020524 A | 1/2010 |
| JP | 2011-070277 A | 4/2011 |
| JP | 2014-041486 A | 3/2014 |
| JP | 2014-170979 A | 9/2014 |
| JP | 2015-097000 A | 5/2015 |

OTHER PUBLICATIONS

Japanese Office Action for JP Application No. 2020-114685 dated Aug. 3, 2021 with English Translation.
Frederick R. Bieber et al. (Finding Criminals Through DNA of Their Relatives, 2006) (Year: 2006).
Manfred Kayser (Forensic DNA Phenotyping: Predicting human appearance from crime scene material for investigative purposes, 2015) (Year: 2015).
Nothnagel et al. (Potentials and limits of pairwise kinship analysis using autosomal short tandem repeat loci, 2010) (Year: 2010).
Karen Norrgard (Forensics, DNA Fingerprinting, and CODIS, 2006) (Year: 2008).
FBI CODIS (Combined DNA Index System) (Year: 2015).
Steven P. Myers et al, (Searching for first-degree familial relationships in California's offender DNA database; Validation of a likelihood ratio-based approach, 2010) (Year: 2010).

* cited by examiner

FIG. 3

SUSPECT DNA INFORMATION (SAMPLE ID = S01)

| LOCUS | REPEAT NUMBER |
|---|---|
| vWA | 16, 18 |
| FGA | 19, 22 |
| D3S1358 | 15, 16 |
| ... | ... |

FIG. 4

FACIAL IMAGE INFORMATION

| FACIAL IMAGE ID | FACIAL IMAGE | CAMERA LOCATION | DATE |
|---|---|---|---|
| FI01 | FILE A | SECURITY CAMERA A | 2015/1/1 15:53 |
| FI02 | FILE B | SECURITY CAMERA B | 2015/1/1 16:30 |
| ... | ... | ... | ... |

FIG. 9A

REGISTERED DNA INFORMATION

| LOCUS | REPEAT NUMBER |
|---|---|
| vWA | 16, 18 |
| FGA | 19, 22 |
| D3S1358 | 15, 16 |
| ... | ... |

FIG. 9B

SUSPECT DNA INFORMATION

| LOCUS | REPEAT NUMBER |
|---|---|
| vWA | 16, 20 |
| FGA | 21, 32 |
| D3S1358 | 15, 30 |
| ... | ... |

FIG. 10

MATCHING JUDGMENT RESULTS

| LOCUS | JUDGMENT |
|---|---|
| vWA | MATCH |
| FGA | NON-MATCH |
| D3S1358 | MATCH |
| . . . | . . . |

FIG. 11

BLOOD-RELATIVE LIST

| REGISTRATION INFORMATION OF PERSONS PRESUMED TO BE BLOOD RELATIVES | PRESUMED RELATIONSHIP |
|---|---|
| REGISTRATION ID = R04 | PARENT OR OFFSPRING |
| REGISTRATION ID = R05 | PARENT OR OFFSPRING |
| REGISTRATION ID = R06 | GRANDPARENT, SIBLING, OR GRANDCHILD |
| REGISTRATION ID = R07 | GRANDPARENT, SIBLING, OR GRANDCHILD |
| ... | ... |

FIG. 13

FACIAL IMAGE INFORMATION

| FACIAL IMAGE ID | FACIAL IMAGE | CAMERA LOCATION | DATE | FIRST FEATURE VECTOR |
|---|---|---|---|---|
| FI01 | FILE A | SECURITY CAMERA A | 2015/1/1 15:53 | FV1 = {F_11, F_12 ...} |
| FI02 | FILE B | SECURITY CAMERA B | 2015/1/1 16:30 | FV2 = {F_21, F_22, ...} |
| ... | ... | ... | ... | ... |

FIG. 14

BLOOD-RELATIVE LIST

| REGISTRATION INFORMATION OF PERSONS PRESUMED TO BE BLOOD RELATIVES | PRESUMED RELATIONSHIP | SIMILAR FACIAL IMAGE |
|---|---|---|
| REGISTRATION ID = R04 | PARENT OR OFFSPRING | N/A |
| REGISTRATION ID = R05 | PARENT OR OFFSPRING | FACIAL IMAGE ID = FI04 |
| REGISTRATION ID = R06 | GRANDPARENT, SIBLING, OR GRANDCHILD | N/A |
| REGISTRATION ID = R07 | GRANDPARENT, SIBLING, OR GRANDCHILD | N/A |
| ... | ... | ... |

SUSPECT INFORMATION

| SAMPLE ID | FACIAL IMAGE | BLOOD RELATIVE INFORMATION |
|---|---|---|
| S03 | <br>ID = FI04 | RELATIONSHIP WITH SUSPECT: PARENT OR OFFSPRING<br>REGISTRATION ID OF BLOOD RELATIVE: R05<br>ADDRESS OF BLOOD RELATIVE: BB CITY, AA PREFECTURE |

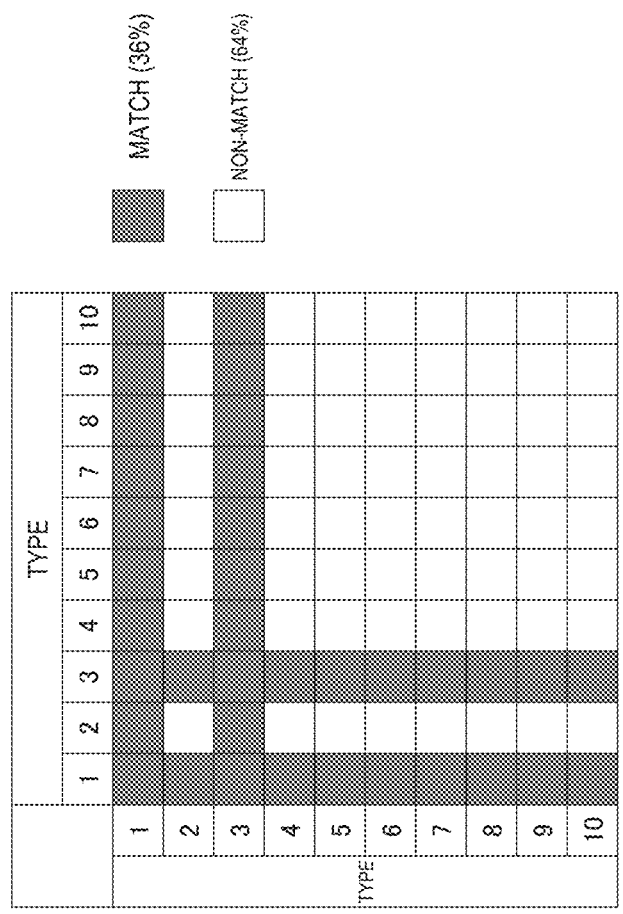

INFORMATION PROCESSING APPARATUS, SUSPECT INFORMATION GENERATION METHOD AND PROGRAM

CROSS-REFERENCE TO RELATED APPLICATIONS

The present application is a continuation application of U.S. patent application Ser. No. 16/079,796 filed on Aug. 24, 2018, which is a National Stage Entry of international application PCT/JP2017/007201 filed on Feb. 24, 2017, which claims the benefit of priority from Japanese Patent Application 2016-035861 filed on Feb. 26, 2016, the disclosures of all of which are incorporated in their entirety by reference herein.

TECHNICAL FIELD

The present invention relates to an information processing apparatus, suspect information generation method and program, and particularly to an information processing apparatus, suspect information generation method and program dealing with information used in a criminal investigation.

BACKGROUND

In a criminal investigation, it is common to obtain DNA (deoxyribonucleic acid) information of a criminal from a bloodstain left at a crime scene and use it to identify the criminal (for instance refer to Patent Literature 1). Further, the United Kingdom has a database of DNA information of criminals and utilizes it with the DNA information obtained in a criminal investigation, like the one described above, to identify the offender.

Furthermore, in recent years, video data captured by security cameras is utilized in criminal investigations. The documents below describe component technologies related to image processing. Patent Literature 2 discloses a technology that extracts a facial image from an input image. Further, Patent Literature 3 discloses a technology that extracts characteristics from an image.
[Patent Literature 1]
Japanese Patent Kokai Publication No. JP-A-H10-115616
[Patent Literature 2]
Japanese Patent Kokai Publication No. JP-P2014-170979A
[Patent Literature 3]
Japanese Patent Kokai Publication No. JP-P2015-097000A

SUMMARY

The following analysis is given from a viewpoint of the present invention. Note that the disclosure of each Patent Literature cited above is incorporated herein in its entirety by reference thereto.

A criminal investigation using the database described above is effective when the offender is a person with a criminal record (i.e., recidivist) registered in the database, however, information useful for identifying the offender cannot obtained when he or she is a first offender.

It is an object of the present invention to provide an information processing apparatus, suspect information generation method, and program that contribute to providing information for facilitating a criminal investigation.

According to a first aspect of the present invention, there is provided an information processing apparatus including an input part that receives DNA information of a suspect and facial image information including information relating to a plurality of facial images; a blood-relative list generation part that identifies DNA information of a person presumed to be a blood relative of the suspect among a plurality of pieces of DNA information registered in a database and generates a list of blood relatives comprising persons who are presumed to be blood relatives of the suspect using the identified DNA information; a similar image search part that calculates degree of similarity between facial images of the persons on the blood-relative list and each of the plurality of facial images included in the facial image information and searches for and retrieves a facial image resembling the facial image of the person on the blood-relative list from the plurality of facial images included in the facial image information on the basis of the calculated degree of similarity; and a suspect information generation part that generates suspect information by associating information relating to the retrieved facial image with information relating to the person on the blood-relative list who resembles the retrieved facial image.

According to a second aspect of the present invention, there is provided a suspect information generation method including receiving DNA information of a suspect and facial image information including information relating to a plurality of facial images; identifying DNA information of a person presumed to be a blood relative of the suspect among a plurality of pieces of DNA information registered in a database and generating a list of blood relatives comprising persons who are presumed to be blood relatives of the suspect using the identified DNA information; calculating degree of similarity between facial images of the persons on the blood-relative list and each of the plurality of facial images included in the facial image information and searching for and retrieving a facial image resembling the facial image of the person on the blood-relative list from the plurality of facial images included in the facial image information on the basis of the calculated degree of similarity; and generating suspect information by associating information relating to the retrieved facial image with information relating to the person on the blood-relative list who resembles the retrieved facial image.

According to a third aspect of the present invention, there is provided a program having a computer execute a process of receiving DNA information of a suspect and facial image information including information relating to a plurality of facial images; a process of identifying DNA information of a person presumed to be a blood relative of the suspect among a plurality of pieces of DNA information registered in a database and generating a list of blood relatives comprising persons who are presumed to be blood relatives of the suspect using the identified DNA information; a process of calculating degree of similarity between facial images of the persons on the blood-relative list and each of the plurality of facial images included in the facial image information and searching for and retrieving a facial image resembling the facial image of the person on the blood-relative list from the plurality of facial images included in the facial image information on the basis of the calculated degree of similarity; and a process of generating suspect information by associating information relating to the retrieved facial image with information relating to the person on the blood-relative list who resembles the retrieved facial image.

Further, this program can be stored in a computer-readable storage medium. The storage medium may be a non-transient one such as a semiconductor memory, hard disk, magnetic storage medium, and optical storage medium. The present invention can be realized as a computer program product.

According to each aspect of the present invention, there is provided an information processing apparatus, suspect information generation method, and program that contribute to providing information for facilitating a criminal investigation.

BRIEF DESCRIPTION OF DRAWINGS

FIG. 3 is a drawing showing an example of suspect DNA information.

FIG. 4 is a drawing showing an example of facial image information.

FIGS. 9A and 9B are drawings showing examples of DNA information.

FIG. 10 is a drawing for explaining the operation of the blood-relative list generation part.

FIG. 11 is a drawing showing an example of a blood-relative list.

FIG. 13 is a drawing in which feature vectors calculated from facial images in the facial image information are reflected in the facial image information shown in FIG. 4.

FIG. 14 is a drawing showing an example of a blood-relative list in which the results of similarity judgment by the similar image search part are reflected.

FIG. 17 is a drawing for explaining the narrowing-down of blood relatives using DNA.

PREFERRED MODES

First, a summary of an exemplary embodiment will be given. Note that drawing reference signs in the summary are given to each element as an example solely to facilitate understanding for convenience, and the description in the summary is not intended to limit the present invention in any way.

Figure 1:
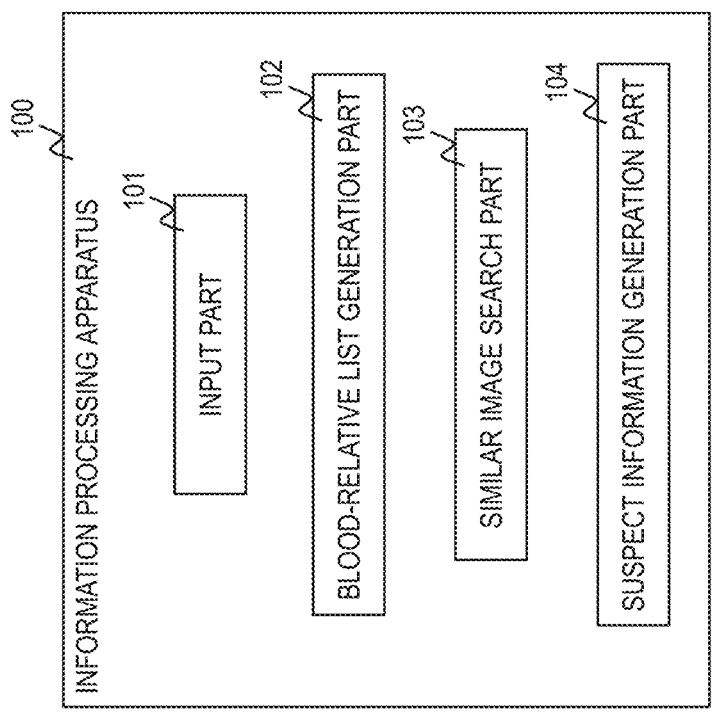
FIG. 1 is a drawing for explaining a summary of an exemplary embodiment.

An information processing apparatus 100 relating to an exemplary embodiment comprises an input part 101, a blood-relative list generation part 102, a similar image search part 103, and a suspect information generation part 104 (refer to FIG. 1). The input part 101 receives DNA information of a suspect and facial image information including information relating to a plurality of facial images. The blood-relative list generation part 102 identifies DNA information of a person presumed to be a blood relative of the suspect among a plurality of pieces of DNA information registered in a database and generates a list of blood relatives comprising persons who are presumed to be blood relatives of the suspect using the identified DNA information. The similar image search part 103 calculates degree of similarity between facial images of the persons on the blood-relative list and each of the plurality of facial images included in the facial image information, and searches for and retrieves a facial image resembling the facial image of the person on the blood-relative list from the plurality of facial images included in the facial image information on the basis of the calculated degree of similarity. The suspect information generation part 104 generates suspect information by associating information relating to the retrieved facial image with information relating to the person on the blood-relative list who resembles the retrieved facial image.

The information processing apparatus 100 treats a person corresponding to DNA information obtained by analyzing a bloodstain, etc., left at a crime scene as a suspect. The information processing apparatus 100 searches for and identifies DNA information of a person presumed to be a blood relative of the suspect among the DNA information stored in the database. Further, the information processing apparatus 100 treats facial image information as information that includes a facial image of the offender in a plurality of facial images obtained from security cameras installed at and around the crime scene, and searches for a facial image of the suspect through the plurality of facial images. More concretely, the information processing apparatus 100 searches for a face resembling the face of a person identified on the blood-relative list through the plurality of facial images, deems the person of the retrieved facial image to be a suspect, and outputs his or her related information (for instance the facial image of the suspect and the names of his or her blood relatives).

As described, the information processing apparatus 100 narrows down persons having a blood relationship with the suspect using DNA information having excellent personal identification capability. Next, assuming that faces of blood relatives resemble each other, the information processing apparatus 100 narrows down persons having faces resembling that of the suspect from persons who were at and around the crime scene. By performing these two stages of narrowing down, the information processing apparatus 100 is able to provide the investigative authority with a facial image of the suspect and information of blood relatives of the suspect from a plurality of facial images obtained from security cameras at and around the crime scene. In other words, since a person likely to have committed a crime is selected from persons who were at and around the crime scene, the information processing apparatus 100 is able to contribute to a criminal investigation in terms of narrowing down suspects on the basis of DNA information of the offender left at the crime scene.

A concrete exemplary embodiment will be described in more detail with reference to the drawings below. It should be noted that the same signs will be given to the same elements in each exemplary embodiment, and the explanation will be omitted.

Exemplary Embodiment 1

A first exemplary embodiment will be described in detail with reference to the drawings.

Figure 2:
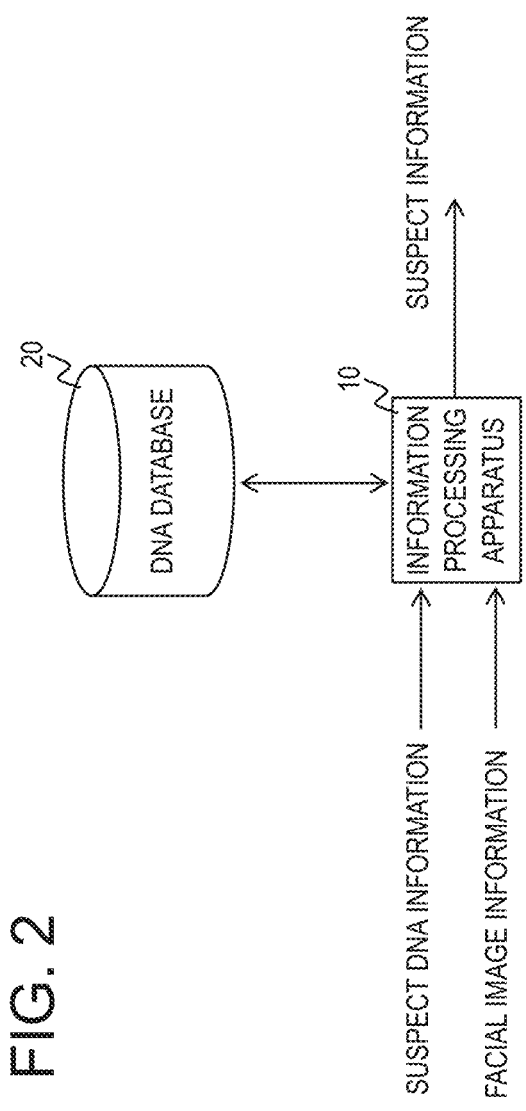
FIG. 2 is a drawing showing a configuration example of a suspect information output system relating to a first exemplary embodiment.

FIG. 2 is a drawing showing a configuration example of a suspect information output system relating to the first exemplary embodiment. In FIG. 2, the suspect information output system includes an information processing apparatus 10 and a DNA database 20. The information processing apparatus 10 and the DNA database 20 are connected via a network (not shown in the drawing).

The information processing apparatus 10 receives suspect DNA information and facial image information. The information processing apparatus 10 generates and outputs suspect information on the basis of these pieces of information and information obtained by accessing the DNA database 20.

The suspect DNA information includes DNA information obtained from DNA analysis of a sample left at a crime scene such as a bloodstain. The DNA information is information that includes the number of STRs (Short Tandem Repeats) in a microsatellite used for personal identification. For instance, the suspect DNA information includes DNA information in which an ID of a sample (Identifier; referred to as "sample ID" hereinafter) taken at the crime scene, the loci of microsatellites (for instance vWA), and the number of repeats are associated (refer to FIG. 3).

The facial image information is information generated from data recorded by video equipment such as security cameras installed at and around the crime scene. For instance, the investigative authority such as the police obtains video data recorded by security cameras installed at and around the crime scene. Then the investigative authority (investigator) extracts facial images of persons in the video data. The investigators generates the facial image information by associating the extracted facial images with information relating to these facial images.

FIG. 4 is a drawing showing an example of the facial image information. In FIG. 4, for instance, the facial image information is generated in such a way that an ID identifying an extracted facial image (referred to as "facial image ID" hereinafter) and the actual file (extracted facial image) are associated with information regarding the location where the person in the extracted facial image was shot (the location of the camera) and date and time in an entry.

Various technologies can be used when facial images are extracted from video data.

For instance, as disclosed in Patent Literature 2, a facial image may be extracted by comparing an input image (video data including a facial image) and a template image of a facial image and seeing whether or not the difference between them is equal to or less than a threshold value. A facial image can also be extracted by having a model combining color information and the directions and densities of edges stored in advance and determining that a face exists when a region similar to the model is detected from an input frame. It is also possible to detect a facial image by using a template created by taking advantage of the fact that the outline of a face (head) is an ellipse and the eyes and the mouth are rectangular shaped. Further, a face detection method utilizing the luminance distribution characteristics in which the cheeks and forehead are high in brightness and the eyes and the mouth are low, or a method that detects a face by utilizing facial symmetry and skin-color region and position may be used. Alternatively, a method in which feature distributions obtained from a large amount of face and non-face learning samples are statistically learned and whether the feature value obtained from an input image belongs to the face or non-face distribution is determined may be used. In other words, a technology relating to machine learning such as a support vector machine may be used to detect a facial image.

The investigators generate the facial image information using a computer capable of the facial image extraction processing described above. It should be noted that the source of the facial images included in the facial image information is not limited to video data; a facial image may be extracted from image data such as a photograph and registered in the facial image information.

Figure 5:
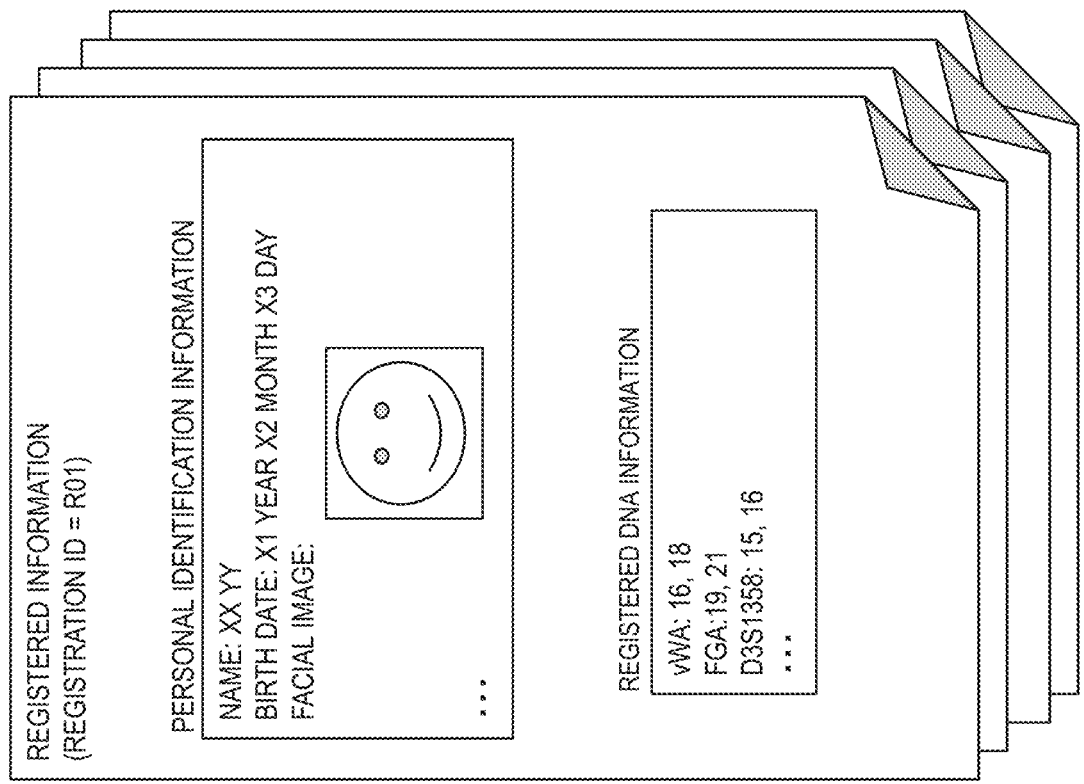
FIG. 5 is a drawing showing an example of information stored in a DNA database relating to the first exemplary embodiment.

The DNA database 20 is an apparatus that stores DNA information of a large amount of people including people with a criminal record (referred to as "registered DNA information" hereinafter) and personal identification information such as facial images while associating one with the other. More specifically, as shown in FIG. 5, the DNA database 20 associates the personal identification information with the registered DNA information and stores these pieces of data. The personal identification information is information used for personal identification such as facial image (photographic portrait), full name, birth date, blood type, ethnicity, skin color, and eye color. The registered DNA information is information that associates the loci of microsatellites (for instance vWA) and the number of STRs (for instance 16, 18). Further, the DNA database 20 may include criminal databases already used in other countries. The information registered in the DNA database 20 will be referred to as "registered information" and an ID identifying each piece of the registered information will be referred to as "registration ID" hereinafter.

The information processing apparatus 10 is an apparatus that generates and outputs suspect information on the basis of the suspect DNA information, the facial image information, and the registered information stored in the DNA database 20.

Figure 6:
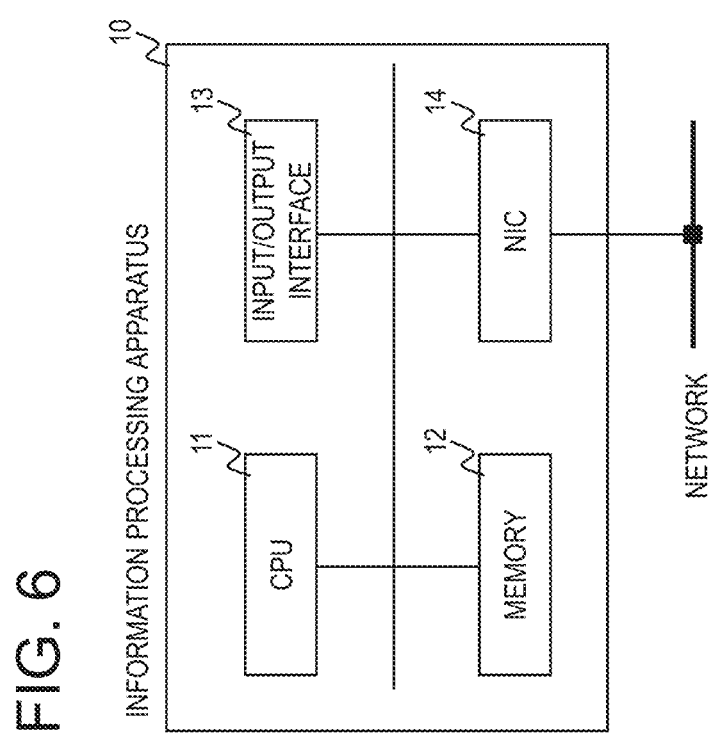
FIG. 6 is a block diagram showing an example of the hardware configuration of an information processing apparatus relating to the first exemplary embodiment.

FIG. 6 is a block diagram showing an example of the hardware configuration of the information processing apparatus 10 relating to the first exemplary embodiment. The information processing apparatus 10 is a computer that comprises the configuration illustrated in FIG. 6. For instance, the information processing apparatus 10 comprises a CPU (Central Processing Unit) 11, a memory 12, an input/output interface 13, and an NIC (Network Interface Card) 14, all connected to each other by an internal bus. The information processing apparatus 10 communicates with the DNA database 20, etc., via the NIC 14. Note that the hardware configuration of the information processing apparatus 10 is not limited by the configuration shown in FIG. 6. The information processing apparatus 10 may include hardware not shown in the drawing.

The memory 12 is a RAM (Random-Access Memory), ROM (Read-Only Memory), or HDD (Hard Disk Drive).

The input/output interface 13 serves as an interface for an input/output apparatus not shown in the drawing. For instance, examples of the input/output apparatus include a display device, operation device, external storage device, and printing device. An example of the display device is a liquid crystal display. Examples of the operation device are a keyboard and mouse. An example of the external storage device includes a USB (Universal Serial Bus) memory.

Figure 7:
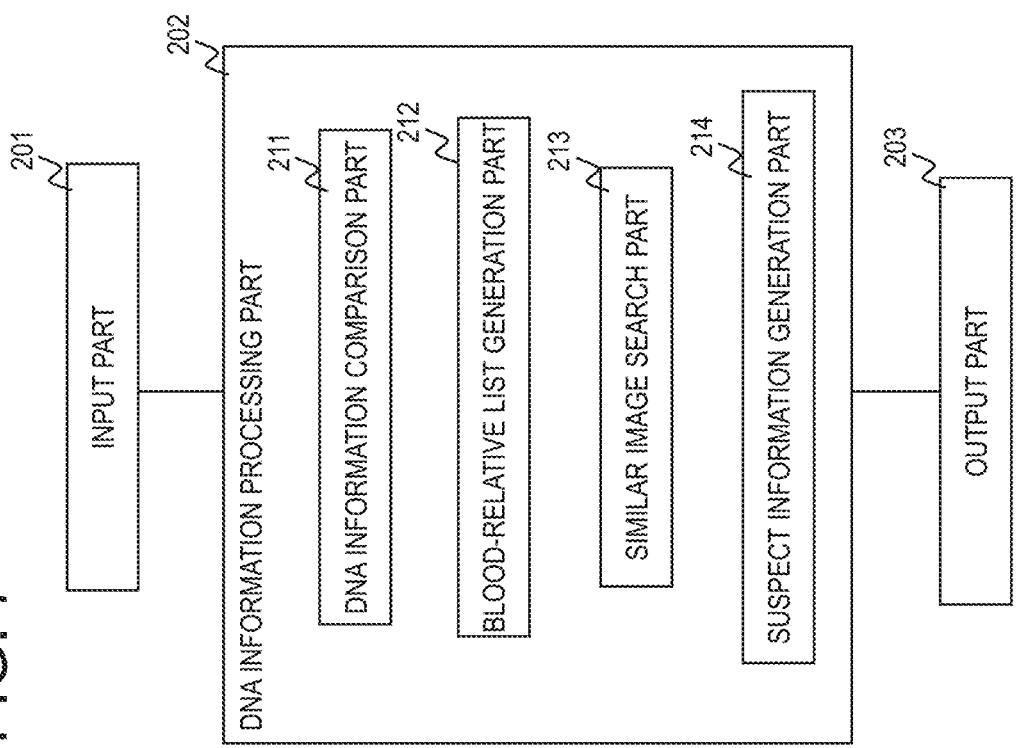
FIG. 7 is a block diagram showing an example of the processing configuration of the information processing apparatus relating to the first exemplary embodiment.

FIG. 7 is a block diagram showing an example of the processing configuration of the information processing apparatus 10 relating to the first exemplary embodiment. In FIG. 7, the information processing apparatus 10 includes an input part 201, a DNA information processing part 202, and an output part 203. For instance, each of these processing module is realized by having the CPU 11 execute a program stored in the memory 12. Further, the program can be downloaded via a network or updated using a storage medium storing the program. These processing modules may be realized by a semiconductor chip. In other words, functions performed by these processing modules may be realized by some kind of hardware and/or software.

The input part 201 receives the suspect DNA information and the facial image information described above. For instance, the input part 201 accesses the external storage device storing the suspect DNA information and the facial image information via the input/output interface 13 and obtains these pieces of information. Alternatively, the input part 201 may obtain the information by accessing a server in a network via the NIC 14. The input part 201 hands over the received suspect DNA information and facial image information to the DNA information processing part 202.

The DNA information processing part 202 generates suspect information on the basis of the suspect DNA information described above. The DNA information processing part 202 includes a DNA information comparison part 211, a blood-relative list generation part 212, a similar image search part 213, and a suspect information generation part 214.

After acquiring the suspect DNA information and the facial image information from the input part 201, the DNA information processing part 202 accesses the DNA database 20 via the NIC 14 and obtains the "registered information" stored in the database. The DNA information processing part 202 starts the DNA information comparison part 211 after having obtained the registered information.

The DNA information comparison part 211 compares the suspect DNA information obtained from the input part 201 and the registered DNA information obtained from the DNA database 20. When an entry in the registered DNA information matching the suspect DNA information is found in the DNA database 20 as a result of the comparison, the DNA information comparison part 211 tells the suspect information generation part 214 that the person corresponding to this entry in the registered DNA information is a suspect and notifies the suspect information generation part 214 of the personal identification information of the person in question. In other words, when an entry in the registered DNA information in the DNA database 20 matches the suspect DNA information, the suspect information generation part 214 is notified that information relating to a suspect is registered in the DNA database 20.

When nothing in the registered DNA information matches the suspect DNA information as a result of comparing the suspect DNA information and the registered DNA information, the DNA information processing part 202 generates suspect information using mainly the blood-relative list generation part 212 and the similar image search part 213.

The blood-relative list generation part 212 identifies DNA information of a person presumed to be a blood relative of a suspect among a plurality of pieces of the registered DNA information registered in the DNA database 20, and generates a list of blood relatives comprising persons who are presumed to be blood relatives of the suspect using the identified DNA information. Specifically, the blood-relative list generation part 212 determines if the loci of microsatellites included in the suspect DNA information match the corresponding loci in the DNA information registered in the DNA database 20, and identifies DNA information of a person presumed to be a blood relative of the suspect according to the ratio of loci determined to match the corresponding loci to the total number of loci on which the matching judgment was performed.

Figure 8:
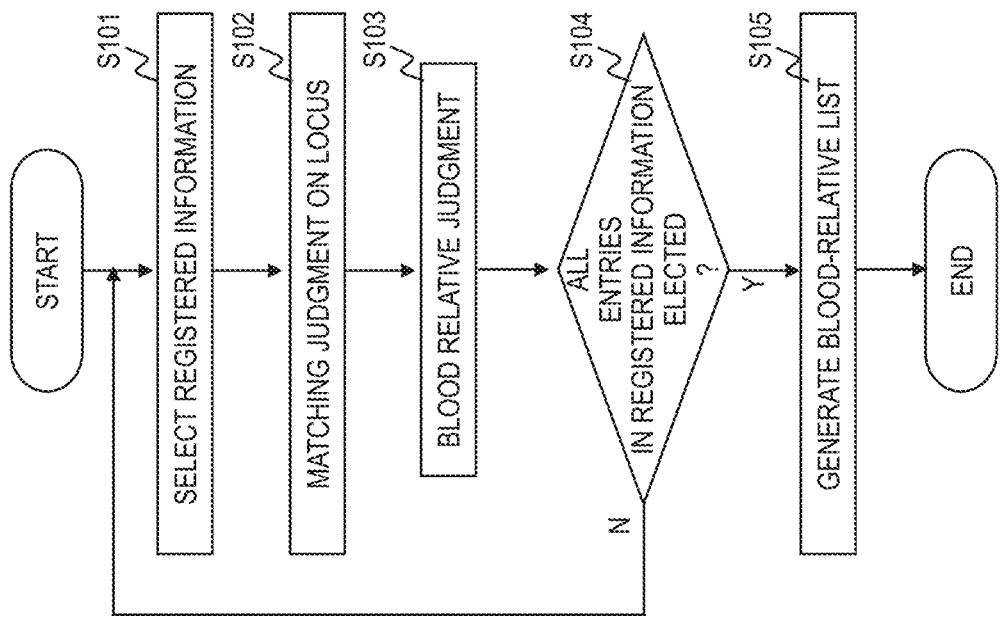
FIG. 8 is a flowchart showing an example of the operation of a blood-relative list generation part.

FIG. 8 is a flowchart showing an example of the operation of the blood-relative list generation part 212. The operation of the blood-relative list generation part 212 will be described with reference to FIG. 8.

In step S101, the blood-relative list generation part 212 selects an entry from a plurality of entries in the registered information obtained from the DNA database 20 (selects a piece of the registered DNA information).

In step S102, the blood-relative list generation part 212 see if the loci of the selected entry in the registered DNA information match the loci of the corresponding suspect DNA information. For instance, let's assume that the selected entry in the registered DNA information is as shown in FIG. 9A and the suspect DNA information FIG. 9B. In this case, as far as the locus vWA is concerned, a repeat number of the locus vWA in the registered DNA information matches a repeat number of the locus vWA in the suspect DNA information (they both have the repeat number 16). As a result, the blood-relative list generation part 212 determines that the locus vWA in the registered DNA information matches another in the suspect DNA information. On the other hand, as far as the locus FGA is concerned, the repeat numbers of the locus FGA in the registered DNA information and the suspect DNA information do not match with each other. Therefore, the blood-relative list generation part 212 determines that the locus FGA in the registered DNA information does not match another in the suspect DNA information. As described, the blood-relative list generation part 212 determines whether or not either one of the two repeat numbers of each locus of a microsatellite included in the suspect DNA information matches either one of the two repeat numbers of the corresponding locus in the registered DNA information.

The blood-relative list generation part 212 repeats the matching judgment processing described above on the loci included in the selected entry of the registered DNA information and comes up with judgment results shown in FIG. 10.

In step S103, the blood-relative list generation part 212 determines whether or not the person corresponding to the selected entry in the registered DNA information is a blood relative of the person corresponding to the suspect DNA information on the basis of the judgment results in the previous step. Specifically, the blood-relative list generation part 212 determines if the person in question is a blood relative according to the ratio of loci determined to match to the total of the loci included in the registered DNA information. For instance, when nearly all loci in the registered DNA information (for instance 95 percent or more) are determined to match, the blood-relative list generation part 212 presumes that the person corresponding to this registered DNA information is a "parent" or "offspring" of the person corresponding to the suspect DNA information. Further, when about half or more loci in the registered DNA information (for instance 45 percent or more but less than 95 percent) are determined to match, the blood-relative list generation part 212 presumes that the person corresponding to this registered DNA information is a "grandparent," "sibling," or "grandchild" of the person corresponding to the suspect DNA information. In other words, by performing threshold processing on the matching judgment results of the registered DNA information, the blood-relative list generation part 212 determines whether or not the person corresponding to this DNA information is a blood relative of the person corresponding to the suspect DNA information and infers the relationship between the two (the registered person in the DNA database 20 and the suspect).

In steps S104, the blood-relative list generation part 212 determines whether or not all entries in the registered information obtained from the DNA database 20 have been selected. If all entries have not been selected, the blood-relative list generation part 212 repeats the processing of the step S101 and the subsequent steps. If all entries have been selected, the blood-relative list generation part 212 executes the processing of step S105.

In the step S105, the blood-relative list generation part 212 organizes the results of the judgments and presumptions regarding blood relatives in the step S103, generates a blood-relative list, and hands the list over to the similar image search part 213. For instance, the blood-relative list generation part 212 generates a blood-relative list as shown in FIG. 11 and gives the list to the similar image search part 213.

The similar image search part 213 searches for a facial image resembling a facial image of a person identified by the blood-relative list through a plurality of facial images included in the facial image information. Specifically, the similar image search part 213 calculates the degree of similarity between the facial image of a person on the blood-relative list and each of the plurality of facial images included in the facial image information, and searches for a facial image resembling the facial image of the person on the blood-relative list from the plurality of facial images included in the facial image information on the basis of the calculated degree of similarity.

Figure 12:
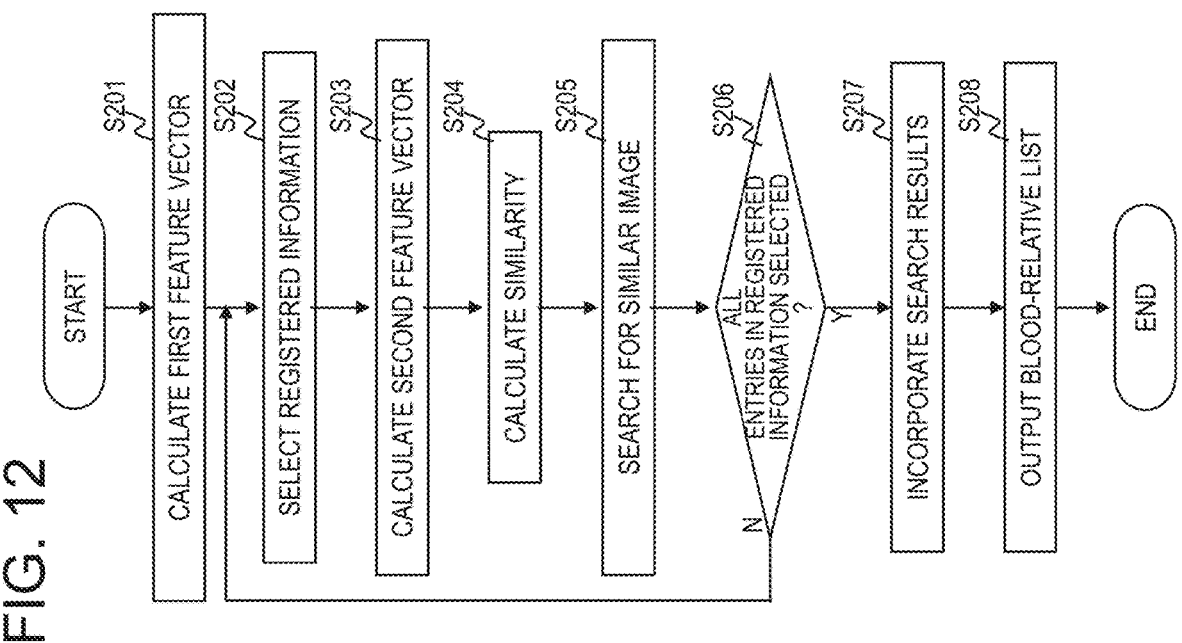
FIG. 12 is a flowchart showing an example of the operation of a similar image search part.

FIG. 12 is a flowchart showing an example of the operation of the similar image search part 213. The operation of the similar image search part 213 will be described with reference to FIG. 12.

In step S201, the similar image search part 213 calculates a feature vector from each facial image of the facial image information. Regarding the feature vector calculation from the facial images, for instance, as disclosed in Patent Literature 3, feature points (such as the center points and end points of the eyes, nose, and mouth) are extracted from the facial images, the positional relationships among the extracted feature points and the gray values and characteristics (periodicity, directionality, color distribution, etc.) around the feature points are calculated as feature values, and these feature values can be arranged (sets of the feather values are created) as a feature vector. Here, different facial images as the sources of the feature vector calculation produce different feature vectors. In other words, the same facial images as the sources of the feature vector calculation produce identical or nearly identical feature vectors. The feature vector calculated from a facial image of the facial image information will be referred to as the first feature vector hereinafter.

Further, as described later, similarities between the first feature vector and another feature vector (referred to as the second feature vector hereinafter) calculated from facial images registered in the DNA database 20 are determined. At that time, it is assumed that the facial images registered in the DNA database 20 are shot in fairly similar conditions (the distance between the camera and the face and the face's angle and direction towards the camera). More specifically, it is assumed that data of frontal facial images shot at a predetermined distance is registered in the DNA database 20. On the other hand, the facial images included in the facial image information were extracted from video data shot by security cameras. Therefore, it is assumed that these facial images were not shot from the front and that the distances between the persons and the cameras vary. In this case, the feature vectors calculated from these two databases may end up being different even if a facial image in the facial image information and a facial image in the DNA database 20 are of the same person. Therefore, it is desired that the first feature vector be calculated after geometrically converting the facial images of the facial image information (for instance, rotating the image so that the face faces the front or enlarging/reducing the size of the image so that the face is of a predetermined size).

Information shown in FIG. 13 can be obtained by associating the first feature vector calculated by the similar image search part 213 with the facial image information shown in FIG. 4.

Further, the order of the feature vector (the number of feature values calculated) can be freely set according to the accuracy of the similarity judgment and the processing amount (calculation amount) described later. Normally, tens to hundreds of feature values are calculated from a single facial image.

In step S202, the similar image search part 213 selects an entry of the registered information that is included in the obtained blood-relative list.

In step S203, the similar image search part 213 calculates the second feature vector from the facial image included in the selected entry of the registered information. At this time, the similar image search part 213 calculates a feature vector having the same elements (the same kinds of feature values) and the same dimension as the first feature vector.

In step S204, the similar image search part 213 calculates the degree of similarity between each of the first feature vectors calculated from the facial images of the facial image information and the second feature vector calculated from the registered information. For instance, the similar image search part 213 calculates the chi-squared distance or the Euclidean distance between the two feature vectors. The calculated chi-squared distance or the Euclidean distance serves as an index indicating the degree of similarity between the two feature vectors (two facial images characterized by the feature vectors). It should be noted that the index indicating the degree of similarity between the two feature vectors is not limited to the Euclidean distance or chi-squared distance; the index may be a correlation value between the two feature vectors.

In step S205, the similar image search part 213 searches for a facial image resembling the facial image included in the registered information (the registered information of the blood-relative list) selected in the step S202 through the plurality of facial images included in the facial image information on the basis of the degree of similarity calculated in the step S204. More specifically, through the plurality of facial images in the facial image information, the similar image search part 213 searches for a facial image having a degree of similarity higher than a predetermined criterion. For instance, in a case where the Euclidean distance or chi-squared distance is used as the indicator of similarity, a facial image included in the facial image information having a value (Euclidean distance or chi-squared distance) less than a predetermined threshold value is determined to resemble the person identified by the blood-relative list and is extracted (retrieved).

In step S206, the similar image search part 213 determines whether or not all entries of the registered information included in the blood-relative list have been selected. If all entries have not been selected, the similar image search part 213 repeats the processing of the step S202 and the subsequent steps. If all entries have been selected, the similar image search part 213 executes the processing of step S207.

In step S207, the similar image search part 213 has the search results in the step S205 reflected in the blood-relative list. For instance, the similar image search part 213 obtains information shown in FIG. 14 by having the results in the step S205 reflected in the blood-relative list shown in FIG. 11.

In step S208, the similar image search part 213 outputs the blood-relative list that incorporates the results of searching for similar facial images to the suspect information generation part 214.

The suspect information generation part 214 generates suspect information.

When receiving a notification from the DNA information comparison part 211 that information regarding a suspect is registered in the DNA database 20, the suspect information generation part 214 incorporates all or some of the personal identification information in the registered information received along with the notification into the suspect information, and hands the information over to the output part 203. In other words, when an entry in the registered DNA information matching the repeat numbers of each locus included in the suspect DNA information is registered in the DNA database 20, the suspect information generation part 214 uses the personal identification information of the person having the DNA information matching the suspect DNA information to generate the suspect information. Specifically, the suspect information generation part 214 deems the person associated with the registered DNA information matching the suspect DNA information to be a suspect and generates the suspect information from his or her registered information (personal identification information: full name, birth date, etc.).

When obtaining the blood-relative list (including information regarding similar facial images) from the similar image search part 213, the suspect information generation part 214 generates the suspect information on the basis of this blood-relative list. Specifically, the suspect information generation part 214 searches for an entry on the obtained blood-relative list having a similar facial image. Then the suspect information generation part 214 generates the suspect information by associating, for instance, a sample ID to be processed, the facial image ID of this searched and retrieved entry, and all or some of the personal identification information relating the registration ID of the retrieved entry.

Figure 15:
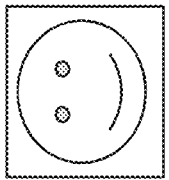
FIG. 15 is a drawing showing an example of suspect information.

For instance, if obtaining the blood-relative list shown in FIG. 14, the suspect information generation part 214 generates the suspect information by associating "Facial Image ID=FI04" in the second entry from the top, the personal identification information obtainable from "Registration ID=R05," and "Presumed Relationship" on the blood-relative list (refer to FIG. 15).

The suspect information generation part 214 hands over the generated suspect information to the output part 203.

The output part 203 outputs the suspect information to the outside. For instance, the output part 203 displays the suspect information on a display device. Alternatively, the output part 203 may output data relating to the suspect information to a printing device and instruct the device to print the data. Furthermore, the output part 203 may output the suspect information via the NIC 14 to a terminal or server connected to a network.

Figure 16:
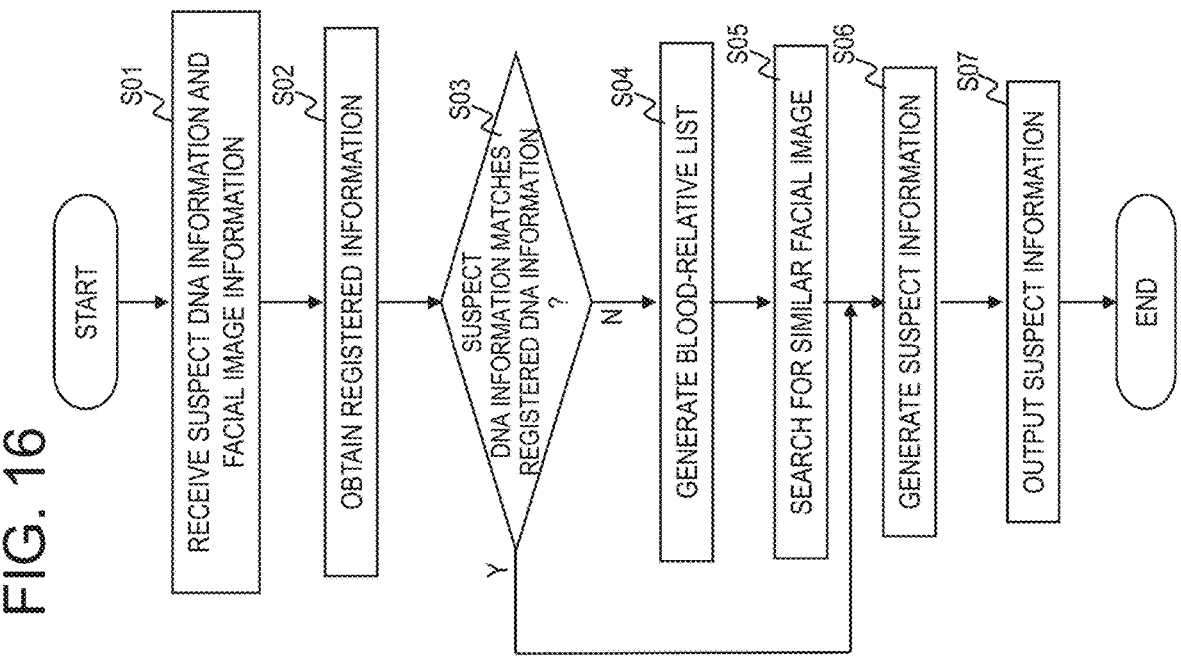
FIG. 16 is a flowchart showing an example of the operation of the information processing apparatus relating to the first exemplary embodiment.

The operation of the information processing apparatus 10 relating to the first exemplary embodiment is summarized in a flowchart shown in FIG. 16.

In step S01, the input part 201 receives the suspect DNA information and the facial image information.

In step S02, the DNA information processing part 202 obtains the registered information by accessing the DNA database 20.

In step S03, the DNA information processing part 211 determines whether or not any registered DNA information in the obtained registered information matches the suspect DNA information. If registered DNA information matching the suspect DNA information exists in the obtained registered information (Yes in the step S03), the operation goes to step S06. If no registered DNA information in the obtained registered information matches the suspect DNA information (No in the step S03), the operation goes to step S04.

In the step S04, the blood-relative list generation part 212 determines if the suspect DNA information matches the registered DNA information and identifies persons presumed to be blood relatives of the suspect among a plurality of persons registered in the DNA database 20 (generating a blood-relative list).

In step S05, the similar image search part 213 calculates the degree of similarity between each facial image included in the facial image information and facial images derived from the blood-relative list, and searches for facial images (similar facial images) resembling the facial images of persons on the blood-relative list.

In the step S06, the suspect information generation part 214 generates the suspect information on the basis of information obtained from the DNA information comparison part 211 or the similar image search part 213.

In step S07, the output part 203 outputs the suspect information to the outside. In other words, the output part 203 provides the investigators with the suspect information useful for criminal investigation.

Further, the blood-relative list generation part 212 detects persons presumed to be blood relatives of the offender, and persons unrelated to the offender (persons who are not relatives) may be detected. However, for instance, in a case where 10 kinds of repeat numbers exist for a locus, 36 percent of persons registered in the DNA database 20 will be determined to match the criminal as far as this locus is concerned. As shown in FIG. 17, conceptually, each person is classified in any one of 100 squares, and when the offender has Types 1 and 3 repeat numbers, persons classified in the 36 shaded squares are determined to match the offender. Here, with an assumption that 10 kinds of repeat numbers exist for each of 20 loci, the possibility of a judgment that all the loci match is $0.36^{20}=1.33\times10-9$, and it is very unlikely that any person unrelated to the offender will be detected as a "parent" or "offspring" of the offender.

As described, upon receiving as a processing request the DNA information of a sample taken at a crime scene, the information processing apparatus 10 relating to the first exemplary embodiment determines whether or not this DNA information (the suspect DNA information) matches the DNA information registered in the DNA database 20 and extrapolates a blood relative of the suspect. Further, the information processing apparatus 10 performs the facial image similarity judgment between the facial images of persons shot by security cameras installed at and around the crime scene and the presumed blood relative, and if any person resembling the presumed blood relative is detected, the information processing apparatus 10 selects the detected person as a highly suspicious person. As a result, the information processing apparatus 10 can contribute to a criminal investigation in terms of narrowing down suspects on the basis of DNA information of the offender left at the crime scene since a highly suspicious person is selected from those who were at and around the crime scene.

It should be noted that the configuration of the suspect information output system (FIG. 2) described in the exemplary embodiment above is an example and the system configuration is not limited thereto. For instance, the information processing apparatus 10 may extract facial images to be included in the facial image information instead of having another apparatus do it. In this case, the investigator provides video data obtained from security cameras to the information processing apparatus 10. Further, when the information processing apparatus 10 extracts facial images, the geometric transformation described above may be performed when the facial images are extracted and the geometric transformation processing thereafter (image normalization processing) may be omitted.

Alternatively, the information processing apparatus 10 may delegate the processing relating to the suspect's blood relatives and the processing of searching for a similar image to an external apparatus. For instance, the DNA database 20 may have the functions of the blood-relative list generation part 212 implemented therein, and the information processing apparatus 10 may be notified of a blood-relative list when the suspect DNA information is provided to the DNA database 20.

Alternatively, the information processing apparatus 10 may obtain the registered information from an internal storage device in addition to an external apparatus such as the DNA database 20. Further, the database accessed by the information processing apparatus 10 is not limited to a single database or domestic databases, and databases created by overseas investigative authorities may be used.

In the exemplary embodiment described above, parents, offspring, grandparents, siblings, and grandchildren are extrapolated as blood relatives of a suspect, however, extrapolated relatives may be enlarged by adjusting the threshold value of the threshold processing on the degree of similarity (to great-grandchildren).

The credibility of presumed relatives and retrieved similar images is not mentioned in the exemplary embodiment described above, however, the reliability of these pieces of information may be generated and reflected in the suspect information.

A single similar facial image is retrieved from a single blood-relative list in the exemplary embodiment described above, however, it stands to reason that a plurality of similar facial images can be retrieved from a single blood-relative list. In other words, a plurality of suspects can be provided from a single sample.

The facial image in the facial image information (the facial image of a suspect) is included in the suspect information in the exemplary embodiment described above, however, a facial image obtained from the DNA database 20 (the facial image of a blood relative) may be included in the suspect information as well. In this case, the investigator can easily compare the facial image of the suspect with that of a blood relative and more useful information can be provided.

In the exemplary embodiment described above, the suspect DNA information obtained from a single sample is provided to the information processing apparatus 10, and the suspect information corresponding to this suspect DNA information is outputted from the information processing apparatus 10. Therefore, when bloodstains from a plurality of persons are taken at a crime scene, the suspect DNA information obtained from each sample is supplied to the information processing apparatus 10 and corresponding suspect information can be obtained. Alternatively, a plurality of pieces of the suspect DNA information may be supplied to the information processing apparatus 10 at once and corresponding pieces of the suspect information may be outputted.

Further, it becomes possible to implement a method for generating suspect information (suspect information generation method) used in a criminal investigation using a computer by having the computer execute the computer program described above.

Further, a plurality of processes (steps) are described in order in the flowcharts used in the description above, however, the execution order of the steps performed in the exemplary embodiment is not limited to the order in the description. The order of the steps shown in the drawings may be rearranged to an extent that the content is not changed. For instance, multiple processes may be performed simultaneously.

The exemplary embodiment above can be summarized as follows without being limited thereto.

[Mode 1]
As the information processing apparatus relating to the first aspect.

[Mode 2]
The information processing apparatus according to Mode 1, wherein
the DNA information includes the number of short tandem repeats in a microsatellite used for DNA identification, and the blood-relative list generation part determines if the loci of microsatellites included in the DNA information of the suspect match the corresponding loci in the DNA information registered in the database and identifies DNA information of a person presumed to be a blood relative of the suspect according to the ratio of loci determined to match the corresponding loci to the total number of loci on which the matching judgment was performed.

[Mode 3]
The information processing apparatus according to Mode 2, wherein
the blood-relative list generation part infers the relationship between a person presumed to be a blood relative and a suspect by performing threshold processing on the ratio of loci determined to match the corresponding loci to the total number of loci on which the matching judgment was performed.

[Mode 4]
The information processing apparatus according to any one of Mode 1 to 3, wherein personal identification information including a facial image and DNA information are registered for each of a plurality of persons in the database.

[Mode 5]
The information processing apparatus according to Mode 4, wherein
the suspect information generation part uses the personal identification information of a person having DNA information matching DNA information of the suspect to generate the suspect information when the DNA information matching the DNA information of the suspect is registered in the database.

[Mode 6]
The information processing apparatus according to Mode 4 or 5, wherein the similar image search part calculates the degree of similarity from a feature vector characterizing the facial images registered in the database and another feature vector characterizing the facial images included in the facial image information.

[Mode 7]
The information processing apparatus according to Mode 6, wherein
the similar image search part calculates Euclidean distance or chi-squared distance as the degree of similarity.
[Mode 8]
As the suspect information generation method relating to the second aspect.
[Mode 9]
As the program relating to the third aspect.
Further, Modes 8 and 9 can be developed into Modes 2 to 7 like Mode 1.

Further, the disclosure of each Patent Literature cited above is incorporated herein in its entirety by reference thereto. It should be noted that other objects, features and aspects of the present invention will become apparent in the entire disclosure and that modifications may be done without departing the gist and scope of the present invention as disclosed herein and claimed as appended herewith. Also it should be noted that any combination of the disclosed and/or claimed elements, matters and/or items may fall under the modifications. Particularly, the ranges of the numerical values used in the present description should be interpreted as a numeric value or small range example included in these ranges even in cases where no explanation is provided.

The invention claimed is:

1. An information processing apparatus, comprising:
at least one memory storing instructions; and
at least one processor configured to execute the instructions to:
acquire input DNA information of a target person;
acquire person images including at least one facial region;
identify DNA information of persons presumed to be a blood relative of the target person from a database including, for each registered person of a plurality of registered persons, a plurality of pieces of registered DNA information of the registered person, a facial image of the registered person, and the ethnic information of the registered person;
after identifying the DNA information of the persons presumed to be the blood relative of the target person from the database, acquire, from the database, ethnic information and facial images of the persons presumed to be the blood relative;
extract feature points from the acquired facial images and feature points from the acquired person images;
compare the feature points extracted from the acquired facial images with the feature points extracted from the person images, yielding a comparison result identify the acquired person images having faces similar to faces in the acquired facial images based on the comparison result; and
output the acquired ethnic information and the acquired person facial images that have been identified as having the faces similar to the faces in the acquired facial images.

2. The information processing apparatus according to claim 1, wherein:
information to be output indicates a reliability of blood relationship between the target person and the blood relative of the target person.

3. The information processing apparatus according to claim 1, wherein
the input DNA information and the registered DNA information include DNA sequence information used for DNA identification, and
the processor is identify the DNA information of the persons presumed to be the blood relative of the target person by executing a matching judgement between loci of a microsatellite included in the input DNA information and corresponding loci of the registered DNA information of each registered person, and select the registered DNA information of each registered person according to a loci ratio that has been determined to match the loci subjected to the matching judgement.

4. The information processing apparatus according to claim 3, wherein
the processor selects relative DNA information by executing information processing on the loci ratio that has been determined to match the loci subjected to the matching judgement.

5. An information processing method, comprising:
acquiring input DNA information which is DNA information of a target person;
acquiring person images including at least one facial region;
identifying DNA information of persons presumed to be a blood relative of the target person from a database including, for each registered person of a plurality of registered persons, a plurality of pieces of registered DNA information of the registered person, a facial image of the registered person, and the ethnic information of the registered person;
after identifying the DNA information of the persons presumed to be the blood relative of the target person from the database, acquiring, from the database, ethnic information and facial images of the persons presumed to be the blood relative;
extracting feature points from the acquired facial images and feature points from the acquired person images;
comparing the feature points extracted from the acquired facial images with the feature points extracted from the person images, yielding a comparison result;
identifying the acquired person images having faces similar to faces in the acquired facial images based on the comparison result; and
outputting the acquired ethnic information and the acquired person facial images that have been identified as having the faces similar to the faces in the acquired facial images.

6. A non-transitory computer-readable recording medium storing a program having a computer execute processing comprising:
acquiring input DNA information which is DNA information of a target person;
acquiring person images including at least one facial region;
identifying DNA information of persons presumed to be a blood relative of the target person from a database including, for each registered person of a plurality of registered persons, a plurality of pieces of registered DNA information of the registered person, a facial image of the registered person, and the ethnic information of the registered person;
after identifying the DNA information of the persons presumed to be the blood relative of the target person from the database, acquiring, from the database, ethnic information and facial images of the persons presumed to be the blood relative;
extracting feature points from the acquired facial images and feature points from the acquired person images;

comparing the feature points extracted from the acquired facial images with the feature points extracted from the person images, yielding a comparison result;

identifying the acquired person images having faces similar to faces in the acquired facial images based on the comparison result; and outputting the acquired ethnic information and the acquired person facial images that have been identified as having the faces similar to the faces in the acquired facial images.

7. The information processing apparatus according to claim 1, wherein the processor is further configured to output a blood-relative list that includes a blood relationship between the target person and the blood relative of the target person.

\* \* \* \* \*